United States Patent [19]
Don Michael et al.

[11] Patent Number: 5,165,396
[45] Date of Patent: Nov. 24, 1992

[54] RESUSCITATION AID

[75] Inventors: T. Anthony Don Michael, Bakersfield, Calif.; Donald R. Gorsuch, Northborough; James G. Nichols, Sturbridge, both of Mass.

[73] Assignee: Brunswick Biomedical Technologies, Inc., Wareham, Mass.

[21] Appl. No.: 823,746

[22] Filed: Jan. 22, 1992

Related U.S. Application Data

[63] Continuation-in-part of Ser. No. 653,638, Feb. 12, 1991, Pat. No. 5,095,898, which is a continuation-in-part of Ser. No. 419,658, Oct. 11, 1989, Pat. No. 4,998,530, which is a continuation-in-part of Ser. No. 202,101, Jun. 1, 1988, abandoned.

[51] Int. Cl.$^5$ ............................................. A61M 16/00
[52] U.S. Cl. ........................... 128/203.11; 128/202.28; 128/207.16
[58] Field of Search ...................... 128/203.11, 207.12, 128/207.16, 202.28, 202.29

[56] References Cited

U.S. PATENT DOCUMENTS

| | | | |
|---|---|---|---|
| 409,954 | 5/1843 | Martindale et al. | 128/146 |
| 1,142,990 | 6/1915 | Stern | 128/203.11 |
| 2,591,953 | 4/1952 | MacLean | 128/146 |
| 2,887,104 | 5/1959 | Suvinsuy et al. | 128/29 |
| 3,252,457 | 5/1966 | Monaco et al. | 128/145.15 |
| 3,957,046 | 5/1976 | Harris | 128/203.11 |
| 4,305,387 | 12/1981 | Reist-Kundle et al. | 128/202.28 |
| 4,328,798 | 5/1982 | Isaacson | 128/202.27 |
| 4,449,526 | 5/1984 | Elan | 128/206.21 |
| 4,573,463 | 3/1986 | Hall | 128/205.24 |
| 4,579,114 | 4/1986 | Gray et al. | 128/203.11 |
| 4,697,587 | 10/1987 | Marinkovich | 128/203.11 |
| 4,819,627 | 4/1989 | Connors | 128/203.11 |
| 4,819,628 | 4/1989 | Eisenbert et al. | 128/203.11 |
| 4,856,506 | 8/1989 | Jinotti | 128/207.16 |
| 4,858,605 | 8/1989 | Levy | 128/203.11 |
| 4,881,540 | 11/1989 | Vigilia | 128/203.11 |
| 4,941,873 | 7/1990 | Irwin | 128/203.11 |
| 4,969,456 | 11/1990 | Cooper | 128/203.11 |
| 4,998,530 | 3/1991 | Don Michael | 128/203.11 |
| 5,088,485 | 2/1992 | Schock | 128/203.11 |
| 5,095,898 | 3/1992 | Don Michael | 128/203.11 |

Primary Examiner—Eugene H. Eickholt
Attorney, Agent, or Firm—Spensley Horn Jubas & Lubitz

[57] ABSTRACT

A medical device for enabling a rescuer to administer mouth-to-mouth resuscitation to a victim while maintaining a sanitary barrier between victim and rescuer, composed of: a sheet of a flexible material forming a barrier to micro-organisms, the sheet being dimensioned to completely cover the victim's mouth and having an opening surrounded by a portion of the sheet which is shaped to allow the rescuer's lips to form an air-tight seal with the victim's lips; a tubular member defining a confined air passage extending through the opening and having a first portion located to be inserted into the mouth of the rescuer and a second portion located to be inserted to the victim's mouth when the sheet is in place; a one-way valve fastened to the tubular member for permitting free passage of air only from the rescuer to the victim; and at least one rigid tubular member associated with the first-recited tubular member and cooperating with the one-way valve in order to render the operation of the valve substantially insensitive to any physical forces applied to the tubular member.

16 Claims, 3 Drawing Sheets

RESUSCITATION AID

CROSS REFERENCE TO RELATED APPLICATION

This is a continuation in part of my copending application Ser. No. 07/653,638, filed on Feb. 12, 1991, now U.S. Pat. No. 5,095,898 entitled RESUSCITATION AID, itself a continuation in part of application Ser. No. 07/419,658, filed on Oct. 11, 1989, entitled RESUSCITATION AID, now U.S. Pat. No. 4,998,530 and itself a continuation in part of my application Ser. No. 07/202,101, filed on Jun. 1, 1988, entitled MASK FOR PERFORMING RESUSCITATION and now abandoned.

BACKGROUND OF THE INVENTION

The present invention relates to an improvement in resuscitation aids, particularly devices for facilitating mouth-to-mouth resuscitation, of the type described in U.S. Pat. No. 4,998,530 and application Ser. No. 07/653,638 now U.S. Pat. No. 5,095,898.

As used herein, mouth-to-mouth resuscitation refers to methods in which air is forced from the lungs of a rescuer into the lungs of a victim of stopped breathing at regular intervals to provide the interchange of air necessary for respiration. If a victim of stopped breathing is to be saved from death, resuscitation must be started promptly after the cessation of breathing. At times, the heart may also have stopped, in which case simultaneous cardiac resuscitation will also be necessary.

Mouth-to-mouth resuscitation, frequently referred to as the "kiss of life", is a technique which is known to a significant portion of the population, particularly since it is not difficult to learn and does not require special equipment.

Unfortunately, the classic mouth-to-mouth technique requires direct contact between rescuer and victim, and many individuals find this aspect of the technique objectionable. Such objections have become even more prevalent because of the fear of transmission of the AIDS virus, given that a victim is often a stranger to a potential rescuer. Because of this fear, even trained paramedic personnel have become reluctant to administer mouth-to-mouth resuscitation.

Many devices have been developed for performing resuscitation in which no mouth-to-mouth contact is required between rescuer and victim. These devices usually involve inserting some type of tube into the airway of a victim. Among these devices are intubation devices, esophageal obturator airways and "bag valve mask" devices.

In order for such devices to be fully effective, they should establish an effective seal over the victim's mouth when air is being breathed into the victim. Many of the known devices are incapable of forming such a seal.

In addition, many known devices are relatively complicated and expensive so that they could not be made widely available for general use. Since resuscitation must be started within minutes after a stoppage of breathing, devices which cannot be made widely available and/or which can only be used by a small number of highly trained personnel are of little practical value.

Thus, mouth-to-mouth resuscitation remains the technique which offers the greatest hope of assistance to a victim of stopped breathing. Because the lips and associated facial muscles of such a victim are flaccid, virtually no known resuscitation aid can produce a perfect seal with the victim's lips. A nearly perfect seal can be created, however, if the rescuer purses his lips and then covers the victim's mouth. Such perfect seal is due in large measure to the ability of the rescuer to close his lips over the mouth area of the victim and thus perfectly conform to that area.

The invention disclosed in U.S. Pat. No. 4,998,530 resolves many of these problems by providing a device which includes: a sheet of a flexible material forming a barrier to micro-organisms, the sheet being dimensioned to completely cover the victim's mouth, the sheet having an opening and a shaped portion which surrounds the opening and is shaped to allow the rescuer's lips to form an air-tight seal with the victim's lips when the rescuer is blowing air into the victim's mouth, the sheet, including the shaped portion, being formed to permit the victim to exhale without obstruction when the rescuer's lips are withdrawn from the sheet; a tubular member defining a confined air passage extending through the opening and having a first portion located to be inserted into the victim's mouth and over the victim's tongue when the sheet is in place and a second portion located to be inserted into the mouth of the rescuer; and means defining a one-way valve fastened to the tubular member for permitting free passage of air only from the rescuer to the victim.

Copending application Ser. No. 07/653,638 is directed to a modification of the embodiment disclosed in U.S. Pat. No. 4,998,530, according to which the valve is supported by the portion of the tubular member which is located to be inserted into the mouth of the rescuer. Since the valve is of a type which is capable of being inadvertently opened by lateral deformation of the tubular member, it was noted that if the valve is supported by the above-described portion of the tubular member, the valve is less likely to be inadvertently opened by deformation forces imposed on the tubular member.

In addition, as disclosed in copending application Ser. No. 07/653,638, proper operation of the valve can be further insured by the provision of a rigid tubular member which preferably extends along at least a substantial part of the tubular member portion which is to be inserted into the mouth of the rescuer and at least a substantial part of the portion of the tubular member which is to be inserted into the victim's mouth and over the victim's tongue when the device is in use. This rigid member serves as a bite block which prevents the victim from closing the air passage and prevents, to a substantial extent, the rescuer from deforming the valve.

However, further study has revealed that under certain circumstances, the valve can be opened by physical deformation of the tubular member which defines the air passage. For example, it has been found possible to manually impose axial forces, or forces having an axial component, on that tubular member which can, under certain circumstances, produce an opening of the valve at a time when the rescuer is not insufflating the victim.

SUMMARY OF THE INVENTION

It is a primary object of the present invention to improve the above-described device.

A more specific object of the invention is to enhance the operating reliability of such a device, particularly in a manner to virtually completely eliminate the possibility of opening of the valve other than during introduction of air or oxygen into the victim.

Another object of the invention is to give the device an effective air flow resistance which encourages the achievement of insufflation periods of optimum duration.

Yet another object of this invention is to create minimum interference with the victim's exhalation activity.

The above and other objects are achieved, according to the present invention, in a medical device for enabling a rescuer to administer mouth-to-mouth resuscitation to a victim while maintaining a sanitary barrier between victim and rescuer, which device includes:

a sheet of a flexible material forming a barrier to micro-organisms, the sheet being dimensioned to completely cover the victim's mouth, the sheet having an opening and a shaped portion which surrounds the opening and is shaped to allow the rescuer's lips to form an air-tight seal with the victim's lips when the rescuer is blowing air into the victim's mouth, the sheet, including the shaped portion, being formed to permit the victim to exhale without obstruction when the rescuer's lips are withdrawn from the sheet;

a first tubular member defining a confined air passage extending through the opening and having a first portion located to be inserted into the mouth of the rescuer and a second portion located to be inserted into the victim's mouth and over the victim's tongue when the sheet is in place; and means defining a one-way valve fastened to the tubular member for permitting free passage of air only from the rescuer to the victim, by the improvement comprising:

a second tubular member of a rigid material held in place relative to said first tubular member to surround the air passage and extending along both said first portion and said second portion of said first-recited tubular member, said second tubular member serving as a bite block to prevent the victim from closing the air passage and to prevent the rescuer from deforming said valve; and a third tubular member of a rigid material fitted around said first portion of said first tubular member so that said first portion of said first tubular member is firmly held between said second and third tubular members in a manner to inhibit a transmission of axial forces along said first tubular member to said valve.

BRIEF DESCRIPTION OF THE DRAWING

FIG. 3b is a side elevational view of the same device as FIG. 3a, taken in a plane perpendicular to the plane of FIG. 3a.

DESCRIPTION OF THE PREFERRED EMBODIMENTS

Figure 1:
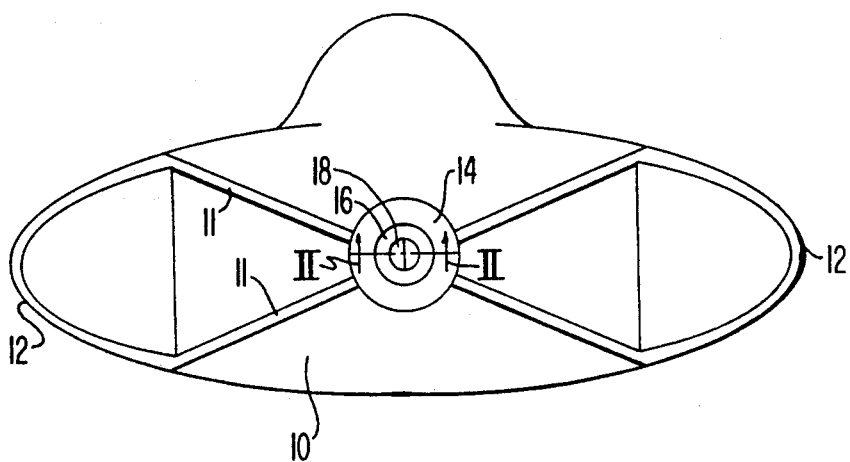
FIG. 1 is an elevational view of a preferred embodiment of a mask according to the present invention.
Figure 2:
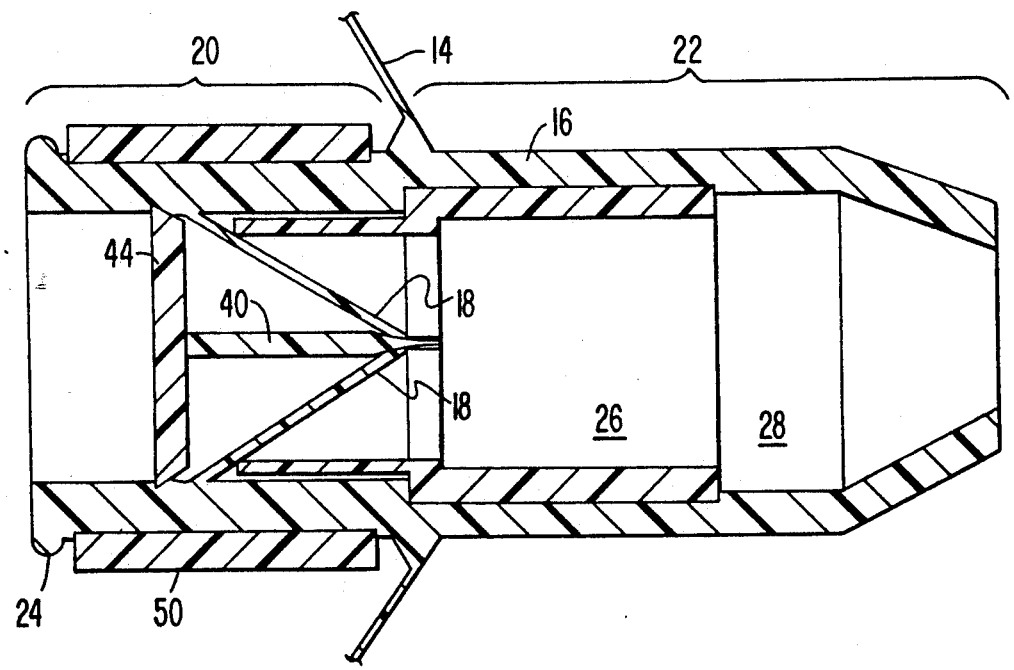
FIG. 2 is a cross-sectional view of the airway portion of the mask of FIG. 1, taken along the line II—II of FIG. 1.

The principal component of the device shown in FIGS. 1 and 2 is essentially a one-piece molded plastic article preferably made of a flexible, transparent or semi-transparent plastic or a clear-to-translucent silicone rubber, the latter material presently being preferred. As shown in FIG. 1, the mask is composed of a generally elliptical cover sheet 10 provided at its ends with straps 12 which are preferably molded integrally with sheet 10. Essentially at the center of sheet 10 there is provided a frustoconical lip portion 14 which is connected to a tube 16 provided with a one-way valve 18 and constituting an airway via which air can be transferred from the rescuer to the victim. In addition, sheet 10 is sized to cover the victim's nostrils. Even though sheet 10 covers the victim's nostrils, it is still necessary for the rescuer to pinch the victim's nose when exhaling into the victim, in accordance with standard CPR practice However, if sheet 10 covers the victim's nostrils, it will serve as a barrier protecting the rescuer from contamination in the event the victim experiences vomiting through the nose during resuscitation.

As shown in FIG. 2, tube 16 and its associated valve 18 are preferably molded integrally with sheet 10 and lip portion 14.

Advantageously, the mask is to be secured in place on the victim, with straps 12 placed around the victim's ears, rather than being worn by the rescuer. Therefore, once tube 16 has been inserted into the victim's mouth and properly positioned, it will remain in place even if the rescuer should remove his mouth from tube 16.

Referring now more specifically to FIG. 2, tube 16 includes a first portion 20 located at the side of the mask which will face the rescuer and a second portion 22 which will be inserted into the victim's mouth at the time the mask is placed on the victim. In the illustrated embodiment valve 18 is supported by portion 20. This represents the location of valve 20 in presently preferred embodiments of the invention. However, because of improvements provided by the subject invention, valve 18 could, if desired, be positioned wholly or partially in portion 22, although such location of valve 18 would complicate manufacture of the device, without creating any apparent offsetting advantage.

Portion 22 is given a length sufficient to assure that it will rest upon the victim's tongue without extending so far as to contact the victim's throat, which would cause gagging, and possible vomiting. It is presently contemplated that this will be achieved if portion 22 has a length of the order of 4 cm. Preferably, portion 20 has a length of the order of 3 cm.

Lip portion 14 constitutes a significant component of the device in that its configuration assures that the rescuer's lips can use lip portion 14 to form a "kiss" which creates an air-tight seal with the victim's lips during the times when the rescuer is blowing air into the victim's mouth, even though the victim's lips are usually flaccid. In effect, the form of lip portion 14 has been painstakingly developed to allow the rescuer's lips to establish an effective seal which makes possible efficient delivery of air to the victim's lungs to an extent comparable to that which can be achieved by direct contact mouth-to-mouth resuscitation.

Moreover, the function of lip portion 14 is such that when the rescuer's mouth is withdrawn, the victim can readily exhale around portion 14. According to a feature of the present invention, exhalation by the victim is facilitated by providing sheet 10 with a plurality of raised ribs 11 which are molded into mask 10 in a manner to protrude from the surface of mask 10 which faces the victim when the device is in use.

The molded member (10, 14, 16, 18) is made of a flexible material, preferably a silicone rubber having a stiffness of 40-75 Durometer, and more preferably 55-70 Durometer. It is presently contemplated that 65 Durometer will provide the best performance. At a stiffness of 65 Durometer, lip portion 14 preferably has a thickness of approximately 0.6 mm. The physical dimensions of the device may be selected to accommodate a large variety of individuals.

As can be seen from both FIGS. 1 and 2, valve 18 is preferably of the type having two flat sides which are designed to meet at a closing line, if no obstacle is present between those sides, the valve thus being of the type which is referred to as a "fish mouth" valve. When a valve of this configuration is made of the type of material described above, one effective example being as described above (65 Durometer silicone rubber, with a wall thickness of the order of 0.5-0.6 mm), it has been found that this valve will open easily to permit the passage of air in the direction from the rescuer to the victim, but will form a tight seal with respect to the transmission of air in the opposite direction. In fact, there is evidence indicating that this valve is impermeable to the transmission of the AIDS virus in the direction from the victim to the rescuer.

At the free end of portion 22, tube 16 extends a sufficient distance to provide a protective enclosure which will reduce the possibility that the victim's tongue can assume a position to block the airway provided by tube 16.

As is shown in FIG. 2, the interior wall of tube 16 has a first diameter at portion 20 and a second diameter, which is larger than the first diameter, over a part of portion 22, the change in diameter occurring essentially at the region where lip portion 14 joins to tube 16 and being defined by an annular shoulder. Associate with tube 16 is a rigid tube 26 which may be constituted, for example, by an acrylic or polycarbonate plastic and which has a thickness sufficient to withstand any biting force which may be produced by the victim. Tube 26 is composed of a cylindrical part which is securely held within portion 22. The axial position of this cylindrical part is accurately determined by the previously-mentioned shoulder at the interior of tube 16 and a land 28 which is also on the inner surface of portion 22 and is spaced from the previously-mentioned shoulder by a distance equal to the axial dimension of the cylindrical part of tube 26.

Tube 26 is further provided with a portion which is of a reduced outer diameter and which has a generally V-shaped cutout to receive valve 18. This reduced diameter portion of tube 26 offers a certain degree of protection to valve 26 against being deformed when a rescuer places his mouth over or grips portion 20. However, it has been found that this protection is not sufficient to prevent undesired opening of valve 18 under some circumstances.

Figure 3A:
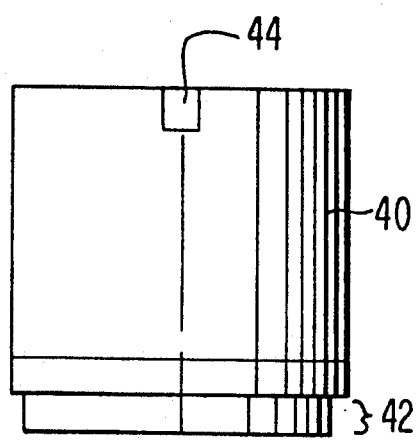
FIG. 3a is a side elevational view of one of the components of the device shown in FIG. 2.
Figure 3B:
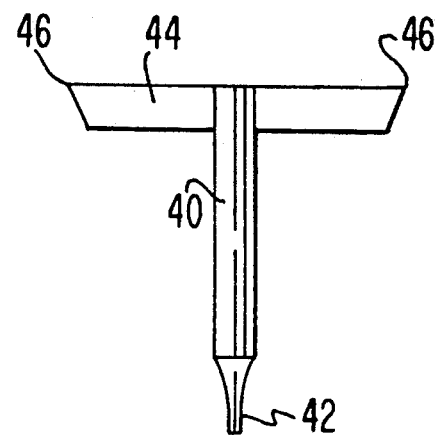
Figure 3C:
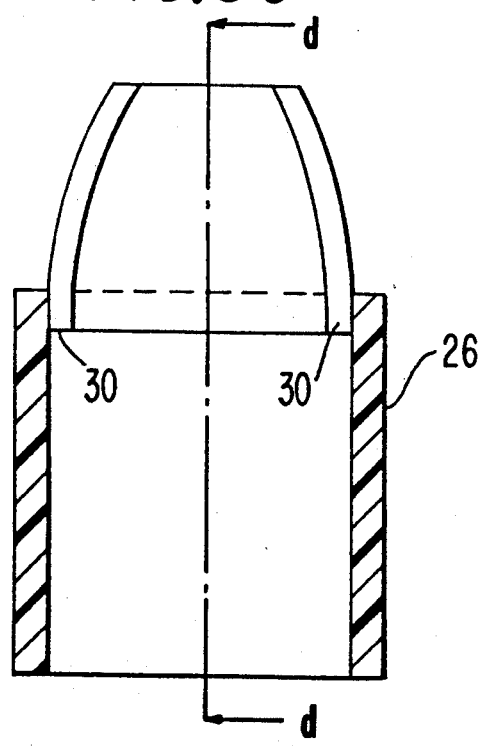
FIG. 3c is a cross-sectional view taken along the line c—c of FIG. 3d of another element of the device shown in FIG. 2.
Figure 3D:
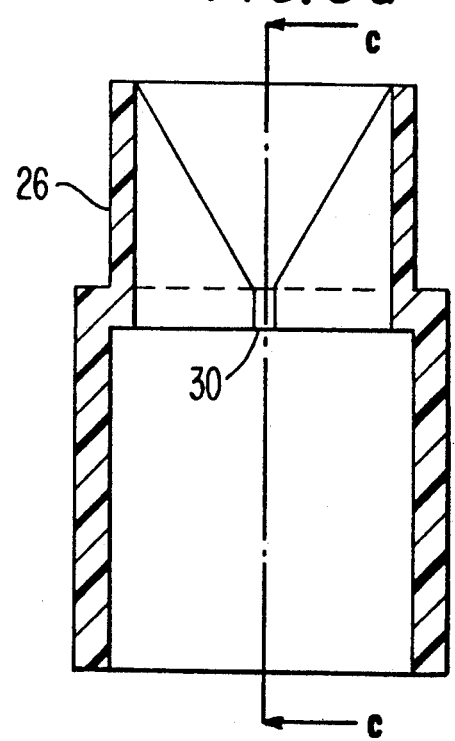
FIG. 3d is a cross-sectional view taken along the line d—d of FIG. 3c.
Figure 3E:
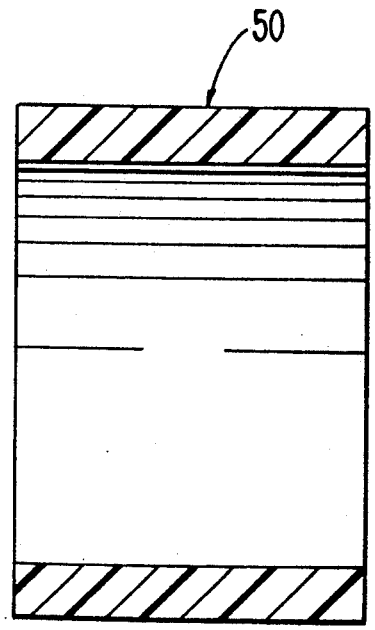
FIG. 3e is a medial cross-sectional view of a further element of the device of FIG. 2.

Therefore, in order to further assure the operating integrity of valve 18, the device is provided, in further accordance with the present invention, with a stiffener plate 40 and a sleeve 50, both of which are made of a rigid plastic, which may be the same material as that employed for tube 26. Two views of stiffener plate 40 are shown in FIGS. 3a and 3b, two views of tube 26 are shown in FIGS. 3c and 3d and a cross-sectional view of sleeve 42 is shown in FIG. 3e. The following description will refer to both FIG. 2 and the appropriate ones of FIGS. 3.

As is apparent from FIG. 2, stiffener plate 40 has a tapered edge 42 whose ends are to be seated in two slots 30 provided in tube 26 at the location where the outer diameter of tube 26 changes. The tapering of edge 42 is visible in FIG. 3b. As shown in FIG. 3a, this tapered edge 42 has a slightly narrower width than the remainder of stiffener plate 40, the width of the remainder of plate 40 being substantially equal to the interior diameter of portion 20 of tube 16.

Stiffener plate 40 carries a cross member 44 having pointed ends 46 which, as shown in FIG. 2, press into tube 16 when member 40 is assembled to tube 26. Cross member 44 is integrally molded with plate 40 and in the assembled state of the device, edge 42 is cemented in slots 30.

Since cross member 44 firmly engages portion 20 of tube 16 and is disposed at the opposite side of valve 18 from tube 26, and since plate 44 is permanently cemented to tube 26, at slots 30, tube 26 is reliably retained in tube 16, regardless of the forces which may be imposed on the device when in use.

Plate 40 is given a width substantially equal to the inner diameter of portion 20 of tube 16. A region of plate 40 which is adjacent edge 42, and which is also tapered, extends between the free ends of the two sides of valve 18, and thus forces these free ends slightly apart. In addition, the width dimension of plate 40, which is the horizontal dimension in FIG. 3a, is selected, as noted above, so that it effects a slight stretching of valve 18 in a direction perpendicular to the plane of FIG. 2. These two actions, the slight separation of the two sides of valve 18 and the stretching of the valve in the direction perpendicular to the plane of FIG. 2, cause the free ends of the valve sides to press against the tapered portion of plate 40 with a closing force which is at least slightly greater than the closing force which would exist between the two sides of the valve if plate 40 were not present. As a result, at those times when the valve is to be closed, a seal which is both tight and reliable is achieved.

The part of tube 26 which is associated with portion 20, plate 40 and cross member 44 cooperate to assure that virtually any deformation force applied to tube 16, including axial forces applied to the free end of portion 20, will not have the effect of opening valve 18.

The security of valve 18 is further aided by the action of sleeve 50 which, as shown in FIG. 2, is dimensioned to effect a slight radial compression of portion 20 of tube 16, to thereby effect a more secure engagement between tube 16 and both the ends of bar 44 and plate 40. Sleeve 50 is retained in place by bead 24.

Because sleeve 50 produces a radial compression of portion 20 of tube 16, it further reduces the chances of inadvertent opening of valve 18 in response to deformation forces applied to the device, and particularly to the free end of portion 20. Sleeve 50 further helps to mechanically unite the pieces 16, 26, 40, 44 and 50 into a relatively rigid structure which ensures that the entire air passage will be kept operational and will not be adversely affected by any forces which may be imposed on the device.

In general, the outer diameter of tube 16 will be selected on the basis of anatomical considerations including, inter alia, the largest diameter which can be easily and comfortably introduced into the mouth of a victim who is either unconscious or is in distress. The diameter of the tube 16 is also selected on the basis of a consideration of the extent to which the victim's mouth should be open in order to be able to form a seal with lip portion 14. Once the outer diameter of tube 16 has been selected, the cross-sectional area of the air passage therein will be determined by the thickness of the parts making up the device, in this case the thicknesses of tubes 16 and 26. In addition, in the device according to the present invention, the effective cross section of the airway will be reduced by the presence of plate 40 and cross member 44. The flow resistance of the passageway will further be influenced by the force needed to open valve 18 and, as noted above, one feature of the structure according to the present invention is that it establishes a higher opening force than heretofore existed. Therefore, plate 40 and member 44 have the effect of reducing the flow cross section within tube 16 and of increasing the flow resistance offered by valve 18.

While these effects may at first glance be considered undesirable, it is believed that, in fact, they are advantageous in view of recent determinations that the duration of each insufflation period occurring during resuscitation should be longer than previously believed to have maximum effect on the victim. Specifically, while it was previously believed that each insufflation period should have a duration of one second, recent studies tend to suggest that an insufflation period of 1.5 seconds, and perhaps somewhat longer, are preferable. It is believed that the presence of plate 40 and, to a limited extend member 44, in the air passage defined by tube 16 has the effect of causing one who is trained in CPR to perform resuscitation with insufflation periods in the vicinity of 1.5 seconds.

Generally, tube 16 has a circular cross section and it is particularly preferred that at least portion 20 have this cross section so that the rescuer can grip portion 20 in his mouth with his head having any orientation relative to that of the victim.

If, during a resuscitation procedure, the victim should experience vomiting, this can be dealt with by removing one of the straps 12 and pulling tube 16 out of the victim's mouth. Since the other strap 12 remains in position, the mask can be easily reinserted after the vomiting episode has terminated.

One feature of a mask according to the present invention is that it does not include any parts which completely obturate the victim's nose or which must be fit over the victim's chin, so that installation of the mask is simplified.

When, as is preferred, sheet 10 is made of a transparent or semitransparent material, observation of the victim's condition is facilitated.

Embodiments of the invention could also be constructed to include an opening for connection of an auxiliary air supply device and/or to include electrodes via which impulses could be supplied to the victim's tongue and/or lips to perform a cardiac pacing or defibrillation function.

Embodiments of the invention may be packaged with a cylindrical metal electrode connected to a wire for use, together with a second electrode, to effect defibrillation, or cardiac pacing. The electrode may be opened or closed at its distal end and can be used while mounted on portion 22 of tube 16 or by itself. When the electrode is open at its distal end and is installed on tube 16, defibrillation or pacing can be performed simultaneously with resuscitation. The second electrode may be connected to any suitable location on the victim's body.

Figure 4:
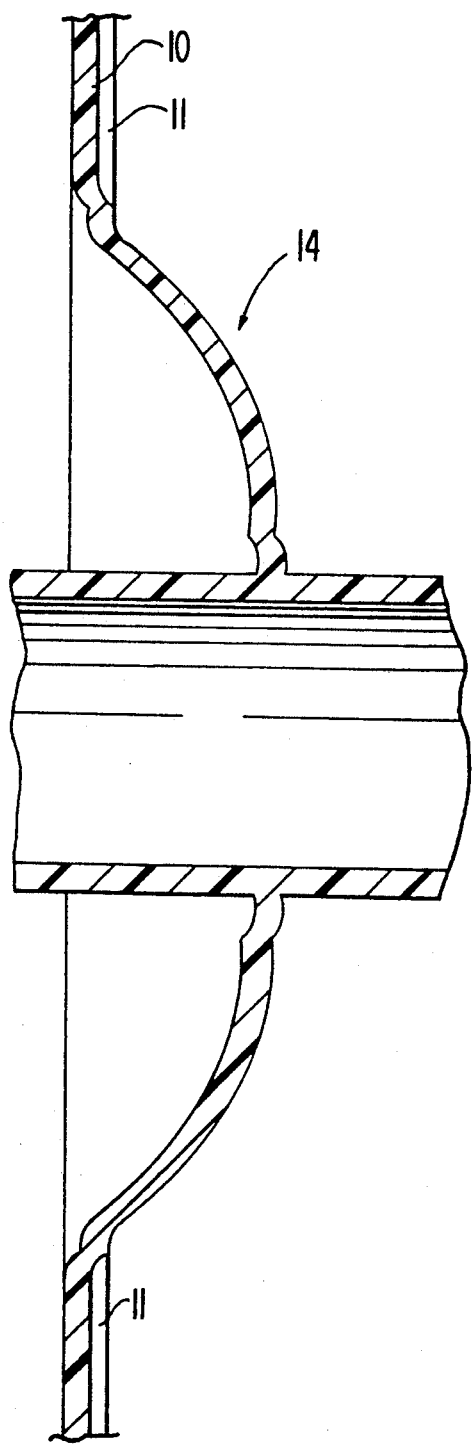
FIG. 4 shows a section of lip portion as it would appear deformed in use.

Referring now to FIG. 4, there is shown the configuration assumed by lip portion 14 when the mask is positioned to perform a resuscitation procedure. At this time, sheet 10 rests against the victim's face so that lip portion 14 flexes. Sheet 10 is formed, by molding, so that the inner and outer peripheries of lip portion 14 form sharply defined angles with adjacent parts of sheet 10. As a result, when sheet 10 rests against the victim's face, lip portion 14 takes on a bowed, or arcuate, shape which is concave toward the victim's mouth and tends to encompass the victim's lips.

It will be noted that in the embodiment illustrated in this application, the opening plane, or line, of valve 18 has been rotated by 90° relative to the orientation shown in the prior copending application. At least when the device according to the invention has the structure shown in FIG. 2, i.e. is provided with both tube 26 and sleeve 50, the operation of valve 18 will not be influenced by its orientation.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. In a medical device for enabling a rescuer to administer mouth-to-mouth resuscitation to a victim while maintaining a sanitary barrier between victim and rescuer, which device includes:

a sheet of a flexible material forming a barrier to micro-organisms, said sheet being dimensioned to completely cover the victim's mouth, said sheet having an opening and a shaped portion which surrounds said opening and is shaped to allow the rescuer's lips to form an air-tight seal with the victim's lips when the rescuer is blowing air into the victim's mouth, said sheet, including said shaped portion, being formed to permit the victim to exhale without obstruction when the rescuer's lips are withdrawn from said sheet;

a first tubular member defining a confined air passage extending through said opening and having a first portion located to be inserted into the mouth of the rescuer and a second portion located to be inserted into the victim's mouth and over the victim's tongue when said sheet is in place; and means defining a one-way valve fastened to said tubular member for permitting free passage of air only from the rescuer to the victim, the improvement wherein said device further comprises:

a second tubular member of a rigid material held in place relative to said first tubular member to surround the air passage and extending along both said first portion and said second portion of said first-recited tubular member, said second tubular member serving as a bite block to prevent the victim from closing the air passage and to prevent the rescuer from deforming said valve; and a third tubular member of a rigid material fitted around said first portion of said first tubular member so that said first portion of said first tubular member is firmly held between said second and third tubular members in a manner to inhibit a transmission of axial forces along said first tubular member to said valve.

2. A device as defined in claim 1 wherein said valve comprises two generally planar, thin, flexible portions which will meet at a closing line when no external forces are applied to said valve and no obstacle is present between said flexible portions, and said device further comprises means defining a stiffening plate having two opposed surfaces and held in position in said device so as to extend between said two sides of said valve and across said closing line so that said two sides of said valve are maintained separated from one another by said plate while normally being in contact with said plate in order to form a tight seal between each said side and a respective surface of said plate.

3. A device as defined in claim 2 wherein said plate has a width substantially equal to the length of the closing line so that said plate imposes a stretching force on said sides of said valve along, and in the direction parallel to the length of, said closing line.

4. A device as defined in claim 1 wherein said sheet, said tubular member and said valve are constituted by a one-piece molded member.

5. A device as defined in claim 4 wherein said molded member is of a material which is flexible over a wide temperature range.

6. A device as defined in claim 5 wherein said molded member is of a silicone rubber.

7. A device as defined in claim 6 wherein said silicone rubber is a 40-75 Durometer silicone rubber.

8. A device as defined in claim 1 wherein said sheet is at least semitransparent.

9. In a medical device for enabling a rescuer to administer mouth-to-mouth resuscitation to a victim while maintaining a sanitary barrier between victim and rescuer, which device includes:

a sheet of a flexible material forming a barrier to micro-organisms, said sheet being dimensioned to completely cover the victim's mouth, said sheet having an opening and a shaped portion which surrounds said opening and is shaped to allow the rescuer's lips to form an air-tight seal with the victim's lips when the rescuer is blowing air into the victim's mouth, said sheet, including said shaped portion, being formed to permit the victim to exhale without obstruction when the rescuer's lips are withdrawn from said sheet;

a first tubular member defining a confined air passage extending through said opening and having a first portion located to be inserted into the mouth of the rescuer and a second portion located to be inserted into the victim's mouth and over the victim's tongue when said sheet is in place; and means defining a one-way valve fastened to said tubular member for permitting free passage of air only from the rescuer to the victim, said valve being composed of two generally planar, thin, flexible portions which will meet at a closing line when no external forces are applied to said valve, the improvement wherein said device further comprises means defining a stiffening plate having two opposed surfaces and held in position in said device so as to extend between said two sides of said valve and across said closing line so that said two sides of said valve are maintained separated from one another by said plate while normally being in contact with said plate in order to form a tight seal between each said side and a respective surface of said plate.

10. A device as defined in claim 9 further comprising a rigid cross member secured to said stiffening plate, extending perpendicular to said surfaces of said stiffening plate, and engaging said first portion of said first tubular member in order to be held in place relative to said tubular member.

11. A device as defined in claim 9 wherein said plate has a width substantially equal to the length of the closing line so that said plate imposes a stretching force on said sides of said valve along, and in the direction parallel to the length of, said closing line.

12. A device as defined in claim 9 wherein said sheet, said tubular member and said valve are constituted by a one-piece molded member.

13. A device as defined in claim 12 wherein said molded member is of a material which is flexible over a wide temperature range.

14. A device as defined in claim 13 wherein said molded member is of a silicone rubber.

15. A device as defined in claim 14 wherein said silicone rubber is a 40-75 Durometer silicone rubber.

16. A device as defined in claim 9 wherein said sheet is at least semitransparent.

* * * * *